US 11,306,057 B2

(12) United States Patent
Silver

(10) Patent No.: US 11,306,057 B2
(45) Date of Patent: *Apr. 19, 2022

(54) ISOTHIOCYANATE FUNCTIONAL SURFACTANTS, FORMULATIONS INCORPORATING ISOTHIOCYANATE FUNCTIONAL SURFACTANTS AND ASSOCIATED METHODS FOR TREATING BIOFILMS

(71) Applicant: Michael E. Silver, Lake City, MI (US)

(72) Inventor: Michael E. Silver, Lake City, MI (US)

(73) Assignee: The William M. Yarbrough Foundation, Peoria, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/878,507

(22) Filed: May 19, 2020

(65) Prior Publication Data
US 2021/0024463 A1    Jan. 28, 2021

Related U.S. Application Data

(63) Continuation of application No. 16/411,398, filed on May 14, 2019, now Pat. No. 10,654,799, which is a continuation of application No. 15/890,578, filed on Feb. 7, 2018, now Pat. No. 10,287,246, which is a continuation of application No. 15/786,757, filed on Oct. 18, 2017, now Pat. No. 10,273,205, which is a continuation-in-part of application No. 15/353,260, filed on Nov. 16, 2016, now Pat. No. 9,962,361, which is a continuation of application No. 15/297,304, filed on Oct. 19, 2016, now Pat. No. 9,951,005, which is a continuation of application No. 14/594,788, filed on Jan. 12, 2015, now Pat. No. 9,951,003, which is a continuation of application No. 13/342,516, filed on Jan. 3, 2012, now Pat. No. 8,933,119.

(60) Provisional application No. 61/502,067, filed on Jun. 28, 2011, provisional application No. 61/429,325, filed on Jan. 3, 2011.

(51) Int. Cl.

| C07C 331/20 | (2006.01) |
| A61K 31/26 | (2006.01) |
| A61P 31/00 | (2006.01) |
| A61P 31/04 | (2006.01) |
| A61K 31/198 | (2006.01) |
| A61K 47/34 | (2017.01) |
| A61K 9/00 | (2006.01) |
| A61K 45/06 | (2006.01) |
| A61K 31/145 | (2006.01) |
| A61K 9/06 | (2006.01) |

(52) U.S. Cl.
CPC .......... *C07C 331/20* (2013.01); *A61K 9/0014* (2013.01); *A61K 31/145* (2013.01); *A61K 31/198* (2013.01); *A61K 31/26* (2013.01); *A61K 45/06* (2013.01); *A61K 47/34* (2013.01); *A61K 9/06* (2013.01); *A61K 2300/00* (2013.01)

(58) Field of Classification Search
CPC .. C07C 331/20; A61K 31/145; A61K 9/0014; A61K 31/198; A61K 45/06; A61K 47/34; A61K 31/26
USPC ............... 514/514, 562, 563, 625, 663, 665; 558/17
See application file for complete search history.

(56) References Cited

U.S. PATENT DOCUMENTS

| 2,905,701 A | 9/1959 | Nutting et al. |
| 3,108,040 A | 10/1963 | Folkers |
| 3,725,030 A | 4/1973 | Newallis et al. |
| 3,740,435 A | 6/1973 | Newallis et al. |
| 3,969,087 A | 7/1976 | Saito et al. |
| 4,083,836 A | 4/1978 | Anjou et al. |
| 4,158,656 A | 6/1979 | Jones et al. |
| 4,191,752 A | 3/1980 | Kada et al. |
| 4,938,949 A | 7/1990 | Borch et al. |
| 5,114,969 A | 5/1992 | Chung et al. |
| 5,126,129 A | 6/1992 | Wiltrout et al. |
| 5,208,249 A | 5/1993 | Rowe et al. |
| 5,231,209 A | 7/1993 | Chung et al. |
| 5,290,578 A | 3/1994 | Passey et al. |

(Continued)

FOREIGN PATENT DOCUMENTS

| CN | 101091705 | 12/2007 |
| EP | 0998943 | 5/2000 |
| EP | 1 961 418 | 8/2008 |
| JP | 2000169321 | 6/2000 |

(Continued)

OTHER PUBLICATIONS

Amara et al. J. Am. Chem. Soc. 2009, 131, 10610-10619.*

(Continued)

*Primary Examiner* — Irina Neagu
(74) *Attorney, Agent, or Firm* — King & Partners, PLC

(57) ABSTRACT

The present invention relates to methods, formulations, and compositions for the treatment of biofilms. In particular, the application discloses isothiocyanate functional surfactants either alone or combination with adjunct agents to treat biofilms. One suitable isothiocyanate functional surfactant is represented by the following chemical structure:

$$H_3C-(CH_2)_{10}-\underset{O}{\overset{\|}{C}}-\underset{H}{\overset{}{N}}-\underset{(CH_2)_4}{\overset{}{CH}}-\underset{O}{\overset{\|}{C}}-OH$$
$$\underset{N=C=S}{}$$

8 Claims, No Drawings

(56) References Cited

U.S. PATENT DOCUMENTS

| | | |
|---|---|---|
| 5,385,734 A | 1/1995 | Friedman |
| 5,411,986 A | 5/1995 | Cho et al. |
| 5,582,818 A | 12/1996 | Nakanishi et al. |
| 5,589,504 A | 12/1996 | Dannenberg et al. |
| 5,686,108 A | 11/1997 | Pusateri et al. |
| 5,725,895 A | 3/1998 | Fahey et al. |
| 5,882,646 A | 3/1999 | Pusateri et al. |
| 5,968,505 A | 10/1999 | Fahey et al. |
| 5,968,567 A | 10/1999 | Fahey et al. |
| 6,008,260 A | 12/1999 | Pezzuto et al. |
| 6,046,231 A | 4/2000 | Kosmeder, II et al. |
| RE36,784 E | 7/2000 | Cho et al. |
| 6,166,003 A | 12/2000 | Lam |
| 6,172,250 B1 | 1/2001 | Seguin et al. |
| 6,177,122 B1 | 1/2001 | Fahey et al. |
| 6,242,018 B1 | 6/2001 | Fahey et al. |
| 6,340,784 B1 | 1/2002 | Mithen et al. |
| 6,348,220 B1 | 2/2002 | Ribnicky et al. |
| 6,414,037 B1 | 7/2002 | Pezzuto et al. |
| 6,436,450 B1 | 8/2002 | Omary et al. |
| 6,455,554 B1 | 9/2002 | Dull et al. |
| 6,465,512 B2 | 10/2002 | Nakamura et al. |
| 6,492,399 B1 | 12/2002 | Dull et al. |
| 6,524,594 B1 | 5/2003 | Santora et al. |
| 6,680,062 B2 | 1/2004 | Muizzuddin et al. |
| 6,737,441 B2 | 5/2004 | Fahey |
| 6,824,796 B2 | 11/2004 | Pusateri et al. |
| 6,878,751 B1 | 4/2005 | Donnelly et al. |
| 6,991,811 B1 | 1/2006 | Brovelli et al. |
| 7,303,770 B2 | 12/2007 | Fahey et al. |
| 7,402,569 B2 | 7/2008 | Fahey |
| 7,407,986 B2 | 8/2008 | Gao et al. |
| 7,615,657 B2 | 11/2009 | Bathurst et al. |
| 7,744,937 B2 | 6/2010 | West et al. |
| 7,820,145 B2 | 10/2010 | Tamarkin et al. |
| 7,879,822 B2 | 1/2011 | Dagan et al. |
| 8,003,633 B1 | 8/2011 | Robertson et al. |
| 8,008,281 B2 | 8/2011 | Prendergast et al. |
| 8,039,511 B2 | 10/2011 | Cheng et al. |
| 8,158,161 B2 | 4/2012 | Sussan et al. |
| 8,168,655 B2 | 5/2012 | Gadek et al. |
| 8,303,949 B2 | 11/2012 | Gao et al. |
| 8,309,541 B1 | 11/2012 | Robertson et al. |
| 8,410,037 B2 | 4/2013 | Molenda et al. |
| 8,492,616 B2 | 7/2013 | Mero |
| 8,510,127 B2 | 8/2013 | Hermann et al. |
| 8,709,406 B2 | 4/2014 | Gao et al. |
| 8,731,970 B2 | 5/2014 | Hermann et al. |
| 8,772,251 B2 | 7/2014 | Morazzoni et al. |
| 8,772,274 B1 | 7/2014 | Robertson et al. |
| 8,835,721 B2 | 9/2014 | Mero |
| 8,865,765 B2 | 10/2014 | Silver |
| 8,865,772 B2 | 10/2014 | Silver |
| 8,921,644 B2 | 12/2014 | Barten |
| 8,933,119 B2 | 1/2015 | Silver |
| 9,017,666 B2 | 4/2015 | Ashurst |
| 9,096,505 B2 | 8/2015 | Robertson et al. |
| 9,096,611 B2 | 8/2015 | Ren et al. |
| 9,126,910 B2 | 9/2015 | Robertson et al. |
| 9,126,911 B2 | 9/2015 | Robertson et al. |
| 9,131,722 B2 | 9/2015 | Kim et al. |
| 9,181,221 B2 | 11/2015 | Ren et al. |
| 9,254,331 B2 | 2/2016 | Dubois et al. |
| 9,308,192 B2 | 4/2016 | Coulombe et al. |
| 9,315,505 B2 | 4/2016 | Ren et al. |
| 9,359,349 B2 | 6/2016 | Ren et al. |
| 9,393,225 B2 | 7/2016 | Beumer et al. |
| 9,504,667 B2 | 11/2016 | Silver |
| 9,532,969 B2 | 1/2017 | Silver |
| 9,636,320 B2 | 5/2017 | Silver |
| 9,642,827 B2 | 5/2017 | Silver |
| 9,771,322 B2 | 9/2017 | Silver |
| 9,828,337 B2 | 11/2017 | Silver |
| 9,839,621 B2 | 12/2017 | Silver |
| 9,931,314 B2 | 4/2018 | Silver |
| 9,932,306 B2 | 4/2018 | Silver |
| 9,949,943 B2 | 4/2018 | Silver |
| 9,951,003 B2 | 4/2018 | Silver |
| 9,951,004 B2 | 4/2018 | Silver |
| 9,951,005 B2 | 4/2018 | Silver |
| 9,962,361 B2 | 5/2018 | Silver |
| 10,080,734 B2 | 9/2018 | Silver |
| 10,111,852 B2 | 10/2018 | Silver |
| 10,273,205 B2 | 4/2019 | Silver |
| 10,287,246 B2 | 5/2019 | Silver |
| 10,308,559 B2 | 6/2019 | Silver |
| 10,308,600 B2 | 6/2019 | Silver |
| 10,335,387 B2 | 7/2019 | Silver |
| 10,343,990 B2 | 7/2019 | Silver |
| 10,654,799 B2 | 5/2020 | Silver |
| 2002/0164381 A1 | 11/2002 | Shacknai et al. |
| 2003/0185864 A1 | 10/2003 | Kobayashi et al. |
| 2003/0198616 A1 | 10/2003 | Howard |
| 2004/0156873 A1 | 8/2004 | Gupta |
| 2005/0042182 A1 | 2/2005 | Arkin et al. |
| 2005/0095261 A1 | 5/2005 | Popp |
| 2005/0100621 A1 | 5/2005 | Popp et al. |
| 2005/0118124 A1 | 6/2005 | Reinhart et al. |
| 2005/0193448 A1 | 9/2005 | Gardner et al. |
| 2006/0127996 A1 | 6/2006 | Fahey |
| 2006/0160713 A1 | 7/2006 | Sekine et al. |
| 2007/0041925 A1 | 2/2007 | Picano et al. |
| 2008/0154210 A1 | 6/2008 | Jordan et al. |
| 2008/0254150 A1 | 10/2008 | Rheins et al. |
| 2008/0306148 A1 | 12/2008 | Robertson et al. |
| 2008/0311192 A1 | 12/2008 | West et al. |
| 2008/0311276 A1 | 12/2008 | West et al. |
| 2009/0081138 A1 | 3/2009 | Ashurst |
| 2009/0186853 A1 | 7/2009 | Yu et al. |
| 2009/0324522 A1 | 12/2009 | Chevreau |
| 2010/0124598 A1 | 5/2010 | West et al. |
| 2011/0003747 A1 | 1/2011 | Coloumbe et al. |
| 2011/0014137 A1 | 1/2011 | Talalay et al. |
| 2011/0028548 A1 | 2/2011 | Fossel |
| 2011/0195103 A1 | 8/2011 | Perez Arcas et al. |
| 2012/0135925 A1* | 5/2012 | Meijler ............ C07D 407/12 514/7.6 |
| 2012/0202878 A1 | 8/2012 | Silver |
| 2013/0116203 A1 | 5/2013 | Rajski et al. |
| 2014/0075590 A1 | 3/2014 | Van Den Bosch et al. |
| 2015/0038579 A1 | 2/2015 | Silver |
| 2015/0126600 A1 | 5/2015 | Silver |
| 2016/0015676 A1 | 1/2016 | Silver |
| 2016/0015677 A1 | 1/2016 | Silver |
| 2016/0022624 A1 | 1/2016 | Silver |
| 2016/0030379 A1 | 2/2016 | Silver |
| 2016/0030380 A1 | 2/2016 | Silver |
| 2016/0030381 A1 | 2/2016 | Silver |
| 2017/0037000 A1 | 2/2017 | Silver |
| 2017/0037001 A1 | 2/2017 | Silver |

FOREIGN PATENT DOCUMENTS

| | | |
|---|---|---|
| JP | 2002284702 | 10/2002 |
| JP | 2008/193572 | 7/2006 |
| WO | WO 1994/005250 | 3/1994 |
| WO | WO 1994/019948 | 9/1994 |
| WO | WO 1997/007230 | 2/1997 |
| WO | WO 1997/026908 | 7/1997 |
| WO | WO 2005/016329 | 2/2005 |
| WO | WO 2006/065736 | 6/2006 |
| WO | WO 2007/056941 | 5/2007 |
| WO | WO 2008/070961 | 6/2008 |
| WO | WO 2009/088986 | 7/2009 |
| WO | WO 2010/140902 | 12/2010 |
| WO | WO 2012/010644 | 1/2012 |
| WO | WO 2012/064973 | 5/2012 |
| WO | WO 2013/003601 | 1/2013 |

OTHER PUBLICATIONS

Zuang et al. Subgroup 2. Skin Irritation/Corrosion, in Cosmetics-European Commission, http://ec.europa.eu/consumers/sectors/

(56) References Cited

OTHER PUBLICATIONS cosmetics/files/doc/antest/(5)_chapter_3/2_skin_irritation_en.pdf., accessed Mar. 13, 2014.
Robert et al. New Engl. J. Med. 1999, 341 (24), 1817-1828.
Weber et al. The Journal of Emergency Medicine, 1999, 17 (2), 235-237.
Saint-Mezard et al. Eur. J. Dermatol. 2004, 14, 284-295.
PCT Written Opinion of the International Searching Authority for International Application No. PCT/US12/44660 dated Jul. 15, 2013.
PCT Written Opinion of the International Searching Authority for International Application No. PCT/US12/44593 dated Sep. 7, 2012.
PCT Written Opinion of the International Searching Authority for International Application No. PCT/US12/44628 dated Apr. 5, 2013.
PCT Written Opinion of the International Searching Authority for International Application No. PCT/US13/052307 dated Dec. 5, 2013.
Yehuda et al., Potential skin anti-inflammatory effects of 4-methylthiobutylisothiocyanate (MTBI) isolated from rocket (Eruca Sativa) seeds, Biofactors 35(3), pp. 295-305, 2009. Abstract; p. 297, Fig. 1. https://www.researchgate.net/publication/24443311_Potential_skin_antiinflammatory_effects_of_4-methylthiobutylisothiocyanate_MTBI_isolated_from_rocket_Eruca_sativa_seeds.
Valentine W. M et al.: "Covalent Cross-Linking of Erythrocyte Spectrin by Carbon Disulfide in Vivo," Toxicology and Applied Pharmacology, Academic Press, Amsterdam, NL, vol. 121, No. 1, Jul. 1, 1993 pp. 71-77.
Sundaram G. S. M. et al.: "Synthesis of Bioorthogonal and Crosslinking Amino Acids for Use in Peptide Synthesis," Amino Acids; The Forum for Amino Acid and Protein Research, Springer-Verlag, VI, vol. 39, No. 5, Apr. 22, 2010, pp. 1381-1384.
Mironov et al.: "Synthesis and Properties of New Chlorin and Bacteriochlorin Photosensitizers," Proceedings of SPIE; Photochemistry; Photodynamic Therapy and Other Modalities. vol. 2625, Jan. 31, 1996, pp. 23-32.
Allyl Isothiocyante Product Safety Data Sheet, sc-252361, pp. 1-14., print date Apr. 22, 2010.
Office Action for U.S. Appl. No. 13/342,516 dated May 22, 2013.
Office Action for U.S. Appl. No. 13/342,516 dated Mar. 18, 2014.
Office Action for U.S. Appl. No. 14/594,788 dated Sep. 30, 2015.
Office Action for U.S. Appl. No. 14/594,788 dated May 17, 2016.
Office Action for U.S. Appl. No. 14/880,408 dated Apr. 6, 2016.
Office Action for U.S. Appl. No. 14/880,408 dated Jul. 25, 2016.
Office Action for U.S. Appl. No. 14/880,408 dated Oct. 18, 2016.
Office Action for U.S. Appl. No. 14/880,418 dated Apr. 7, 2016.
Office Action for U.S. Appl. No. 14/880,418 dated Jul. 19, 2016.
Office Action for U.S. Appl. No. 14/880,418 dated Oct. 18, 2016.
Office Action for U.S. Appl. No. 14/880,426 dated Aug. 8, 2016.
Office Action for U.S. Appl. No. 14/880,426 dated Oct. 31, 2016.
Office Action for U.S. Appl. No. 13/348,821 dated Jan. 16, 2013.
Office Action for U.S. Appl. No. 13/348,821 dated Feb. 25, 2014.
Office Action for U.S. Appl. No. 14/519,462 dated Nov. 30, 2015.
Office Action for U.S. Appl. No. 14/519,462 dated Jul. 14, 2016.
Office Action for U.S. Appl. No. 14/868,897 dated Jun. 27, 2016.
Office Action for U.S. Appl. No. 14/868,929 dated Jul. 7, 2016.
Office Action for U.S. Appl. No. 14/868,959 dated Jul. 7, 2016.
Office Action for U.S. Appl. No. 13/952,236 dated Jun. 23, 2014.
Office Action for U.S. Appl. No. 14/519,510 dated Oct. 16, 2015.
Office Action for U.S. Appl. No. 14/519,510 dated Jun. 8, 2016.
Office Action for U.S. Appl. No. 14/867,585 dated Aug. 18, 2016.
Office Action for U.S. Appl. No. 14/867,626 dated Aug. 19, 2016.
Office Action for U.S. Appl. No. 13/351,616 dated Feb. 21, 2014.
Office Action for U.S. Appl. No. 13/351,616 dated Sep. 18, 2014.
Office Action for U.S. Appl. No. 13/351,616 dated Jan. 29, 2016.
Kricheldorf et al. Makromol. Chem. 1980, 181, 2571-2585.
Office Action for U.S. Appl. No. 14/594,788 dated Jul. 10, 2017.
Office Action for U.S. Appl. No. 14/594,788 dated Jun. 20, 2017.
Office Action for U.S. Appl. No. 14/594,788 dated Apr. 12, 2017.
Office Action for U.S. Appl. No. 14/880,418 dated Sep. 20, 2017.
Office Action for U.S. Appl. No. 15/296,701 dated Jun. 21, 2017.
Office Action for U.S. Appl. No. 15/296,701 dated May 3, 2017.
Office Action for U.S. Appl. No. 15/297,304 dated Jun. 20, 2017.
Office Action for U.S. Appl. No. 15/297,304 dated May 3, 2017.
Office Action for U.S. Appl. No. 15/634,639 dated Aug. 25, 2017.
Office Action for U.S. Appl. No. 15/397,375 dated Sep. 25, 2017.
Office Action for U.S. Appl. No. 15/590,645 dated Jun. 8, 2017.
Office Action for U.S. Appl. No. 15/353,260 dated Aug. 9, 2017.
Office Action for U.S. Appl. No. 15/459,822 dated Oct. 6, 2017.
Office Action for U.S. Appl. No. 15/675,915 dated Nov. 1, 2017.

* cited by examiner

ISOTHIOCYANATE FUNCTIONAL SURFACTANTS, FORMULATIONS INCORPORATING ISOTHIOCYANATE FUNCTIONAL SURFACTANTS AND ASSOCIATED METHODS FOR TREATING BIOFILMS

CROSS-REFERENCE TO RELATED APPLICATIONS

This application is a continuation of U.S. application Ser. No. 16/411,398, entitled "ISOTHIOCYANATE FUNCTIONAL SURFACTANTS, FORMULATIONS INCORPORATING ISOTHIOCYANATE FUNCTIONAL SURFACTANTS AND ASSOCIATED METHODS FOR TREATING BIOFILMS," filed May 14, 2019, now U.S. Pat. No. 10,654,799, which is a continuation of U.S. application Ser. No. 15/890,578, entitled "ISOTHIOCYANATE FUNCTIONAL SURFACTANTS, FORMULATIONS INCORPORATING ISOTHIOCYANATE FUNCTIONAL SURFACTANTS AND ASSOCIATED METHODS FOR TREATING BIOFILMS," filed Feb. 7, 2018, now U.S. Pat. No. 10,287,246, which is a continuation of U.S. application Ser. No. 15/786,757, entitled "ISOTHIOCYANATE FUNCTIONAL SURFACTANTS, FORMULATIONS INCORPORATING ISOTHIOCYANATE FUNCTIONAL SURFACTANTS AND ASSOCIATED METHODS FOR TREATING BIOFILMS," filed Oct. 18, 2017, now U.S. Pat. No. 10,273,205, which is a continuation-in-part of U.S. application Ser. No. 15/353,260, entitled "ISOTHIOCYANATE FUNCTIONAL SURFACTANTS, FORMULATIONS INCORPORATING THE SAME, AND ASSOCIATED METHODS OF USE," filed Nov. 16, 2016, now U.S. Pat. No. 9,962,361, which is a continuation-in-part of U.S. application Ser. No. 15/297,304, entitled "ISOTHIOCYANATE FUNCTIONAL SURFACTANT FORMULATION AND ASSOCIATED METHOD OF USE," filed Oct. 19, 2016, now U.S. Pat. No. 9,951,005, which is a continuation of U.S. application Ser. No. 14/594,788, filed Jan. 12, 2015, now U.S. Pat. No. 9,951,003, which is a continuation of U.S. application Ser. No. 13/342,516, filed Jan. 3, 2012, now U.S. Pat. No. 8,933,119, which claims the benefit of U.S. Provisional Application Ser. No. 61/502,067, filed Jun. 28, 2011, and U.S. Provisional Application Ser. No. 61/429,325, filed Jan. 3, 2011—all of which are hereby incorporated herein by reference in their entirety, including all references cited therein.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to isothiocyanate functional surfactants, formulations incorporating isothiocyanate functional surfactants, and associated methods of use including, but not limited to, the use of isothiocyanate functional surfactants to treat biofilms.

2. Background Art

A biofilm is any group of microorganisms in which cells stick to each other and typically also to a surface. These adherent cells become embedded within a slimy extracellular matrix that is composed of extracellular polymeric substances (EPS). The EPS components are produced by the cells within the biofilm and are typically a polymeric conglomeration of extracellular DNA, proteins, and polysaccharides. Because they have three-dimensional structure and represent a community lifestyle for microorganisms, biofilms are frequently described metaphorically as "cities for microbes."

Biofilms may form on living or non-living surfaces and can be prevalent in natural, industrial and hospital settings. The microbial cells growing in a biofilm are physiologically distinct from planktonic cells of the same organism, which, by contrast, are single-cells that may float or swim in a liquid medium.

Microbes form a biofilm in response to many factors, which may include cellular recognition of specific or non-specific attachment sites on a surface, nutritional cues, or in some cases, by exposure of planktonic cells to sub inhibitory concentrations of antibiotics. When a cell switches to the biofilm mode of growth, it undergoes a phenotypic shift in behavior in which large suites of genes are differentially regulated.

Bacteria growing in biofilms are more resistant to antibiotics and disinfectants than planktonic cells and the resistance increases with the age of the biofilm. Bacterial biofilm also exhibits increased physical resistance towards desiccation, extreme temperatures or light. To be sure, biofilm formation causes industrial, environmental and medical problems and the difficulties in cleaning and disinfection of bacterial biofilm with chemicals is a major concern in many industries. Furthermore, the trend towards milder disinfection and cleaning compositions may increase the insufficient cleaning of surfaces covered with biofilm.

Compositions and formulations for treating biofilms have been known in the art for years and are the subject of a plurality of patents and publications, including, but not limited to: U.S. Pat. No. 9,687,514 entitled "Bacteriophage-Containing Therapeutic Agents," U.S. Pat. No. 9,480,729 entitled "Enzymes for Inhibiting Growth of Biofilms and Degrading Same," U.S. Pat. No. 8,975,275 entitled "Use of Chemotherapeutic Agents," U.S. Pat. No. 7,604,978 entitled "Inhibition of Biofilm Formation," U.S. Pat. No. 7,572,439 entitled "Enzyme Disruption of Bacterial Biofilms," U.S. Pat. No. 6,984,622 entitled "Use of Lipopolysaccharides to Manage Corneal Infections and Wounds," U.S. Pat. No. 6,908,912 entitled "Pyrithione Biocides Enhanced by Zinc Metal Ions and Organic Amines," U.S. Pat. No. 6,100,080 entitled "Method for Enzymatic Treatment of Biofilm," United States Patent Publication Number 2007/0014739 entitled "Compositions and Methods for Controlling Biofilms and Bacterial Infections," and United States Patent Publication Number 2002/0037260 entitled "Compositions for Treating Biofilm"—all of which are hereby incorporated herein by reference in their entirety including the references cited therein.

U.S. Pat. No. 9,687,514 appears to disclose combined phage/antibiotic therapy. More particularly, it relates to use of (i) one or more bacteriophages and (ii) one or more antibiotics in the manufacture of a combined product for simultaneous, separate or sequential administration of (i) and (ii) to treat a bacterial infection characterized by biofilm formation, for example an infection comprising or consisting of *P. aeruginosa*. Treatment in this context may be either therapeutic or prophylactic treatment. Also provided are deposited bacteriophages each exhibiting different strain specificity against *P. aeruginosa* and combinations of such bacteriophages, (e.g., a panel of six deposited bacteriophages which was found to be effective against a high percentage of clinical isolates of *P. aeruginosa* from canine ear infections).

U.S. Pat. No. 9,480,729 appears to disclose enzymes for inhibiting growth of biofilms and degrading biofilms. The enzymes comprise glycosyl hydrolases capable of degrading biofilms. The enzymes are formulated in compositions with and without antimicrobial agents. The enzymes with and without the antimicrobial agents are delivered to biofilms to degrade the biofilms and treat infections of microorganisms associated with the biofilms, delivered to surfaces to inhibit growth of biofilms thereon, and administered to animals to inhibit growth of biofilms therein.

U.S. Pat. No. 8,975,275 appears to disclose the use of chemotherapeutic agents for the production of a medicament for the topical and/or local treatment of diseases caused by bacteria and/or for prophylaxis in humans or animals.

U.S. Pat. No. 7,604,978 appears to disclose compositions and methods for reducing or inhibiting biofilm comprising modulating expression of a cysB gene in a cell. The '978 patent further discloses methods for modulating the expression of a cysB, cysD, cysl, cysJ, cysK, and ybiK as well as methods for identifying gene(s) involved in biofilm formation and for identifying biofilm inhibitors.

U.S. Pat. No. 7,572,439 appears to disclose methods for treating patients in which damaged tissue or an indwelling prosthetic device or catheter has a bacterial biofilm growing thereon, to at least partially disrupt said biofilm, by administering at least one antibacterial enzyme that is lethal or damaging to the biofilm-forming bacteria in an amount that is effective to at least partially disrupt the biofilm upon contact therewith. Methods for prophylactically treating a patient, and methods for disinfecting or sterilizing a surface ex-vivo to remove a biofilm or prevent biofilm growth are also disclosed, as well as implantable articles susceptible to biofilm growth to which a prophylactic coating of an antibacterial enzyme has been applied.

U.S. Pat. No. 6,984,622 appears to disclose the antibiotic polypeptide β-defensin-2 (hBD-2) that is expressed in the eye, and is useful for treating ocular wounds. hBD-2 is increased in the eye upon exposure to lipopolysaccharides (LPS). Administration of LPS to the eye thereby provides a useful method for increasing the amount of this antibiotic peptide in the eye.

U.S. Pat. No. 6,908,912 appears to disclose a stable, soluble, antimicrobial composition concentrate comprising pyrithione or a pyrithione complex in an amount of from about 0.5% to about 30 weight percent, a zinc source in an amount of from about 0.1% to about 10%, and an organic amine component in an amount of from about 30% to about 80%, said percents being based upon the total weight of the composition concentrate. The '912 patent is also directed to methods of controlling the growth of free-living microorganisms or biofilms using the antimicrobial composition of the invention, and products made using the antimicrobial composition of the invention.

U.S. Pat. No. 6,100,080 appears to disclose a method for cleaning and disinfecting a surface at least partly covered by a biofilm layer comprising the steps of contacting the biofilm with a cleaning composition comprising one or more hydrolases, (e.g. a hydrolytic enzyme) produced by a strain of the fungus Aspergillus aculeatus, in an amount effective for either fully or partly removing or releasing the biofilm layer from the surface; and contacting the biofilm with a bactericidal disinfecting composition comprising an oxidoreductase such as an oxidase, a peroxidase or a laccase, in an amount effective for killing the living bacterial cells present in the biofilm. In particular, a disinfecting composition comprising laccase at concentration between about 0.01 to about 1000 mg protein/ml composition and an oxidation enhancer such as methyl syringate.

United States Patent Publication Number 2007/0014739 appears to disclose compounds and compositions useful for controlling bacterial biofilms as well as for controlling and/or preventing bacterial infections. The compounds of the invention are pentacyclic acid triterpenes. Methods for controlling biofilms and for controlling and/or preventing bacterial infections are also disclosed.

United States Patent Publication Number 2002/0037260 appears to disclose a composition for treating a biofilm comprises a first anchor enzyme component to degrade biofilm structures and a second anchor enzyme component having the capability to act directly upon the bacteria for a bactericidal effect.

In addition, natural, semi-sythentic, and/or synthetic compounds having one or more isothiocyanate functional groups and their associated uses have been known in the art for years and are the subject of a plurality of patents and publications, including, but not limited to: U.S. Pat. No. 8,772,251 entitled "Use Of Isothiocyanate Derivatives As Anti-Myeloma Agents," U.S. Pat. No. 7,303,770 entitled "Cancer Chemoprotective Food Products," U.S. Pat. No. 6,737,441 entitled "Treatment Of Helicobacter With Isothiocyanates," U.S. Pat. No. 6,340,784 entitled "Method For Selective Increase Of The Anticarcinogenic Glucosinolates In Brassica Oleracea," U.S. Pat. No. 6,166,003 entitled "Heterocyclic Compounds For Cancer Chemoprevention," U.S. Pat. No. 5,411,986 entitled "Chemoprotective Isothiocyanates," U.S. Pat. No. 5,114,969 entitled "Method Of Inhibiting Lung Tumors, Arylalkyl Isothiocyanates, And Method Of Synthesizing Same," United States Patent Application Publication No. US 2013/0116203 entitled "Isothiocynates And Glucosinolate Compounds And Anti-Tumor Compositions Containing Same," United States Patent Application Publication No. 2009/0081138 entitled "Cancer Chemoprotective Compositions And Natural Oils And Methods For Making Same," and United States Patent Application Publication No. 2006/0127996 entitled "Method Of Extraction Of Isothiocyanates Into Oil From Glucosinolate-Containing Plants And Method Of Producing Products With Oil Containing Isothiocyanates Extracted From Glucosinolate-Containing Plants," all of which are hereby incorporated herein by reference in their entirety—including all references cited therein.

U.S. Pat. No. 8,772,251 appears to disclose the use of glucomoringin (GMG) and its des-thio-glucoside (GMG-ITC) for the preparation of a medicament for the treatment of myeloma. The chemical structures of GMG and GMG-ITC are provided below:

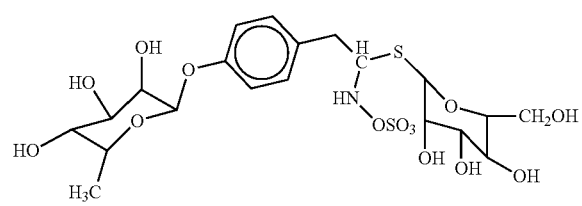

GMG

-continued

GMG-ITC

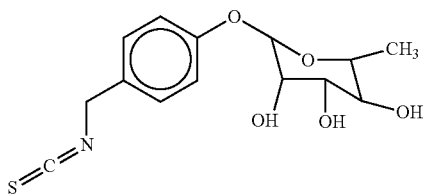

U.S. Pat. No. 7,303,770 appears to disclose vegetable sources that serve as chemoprotective agents. The chemoprotective agents disclosed are rich in glucosinolate (i.e., metabolic precursors to isothiocyanates). The vegetable sources are used to provide a dietary means of reducing the level of carcinogens in mammals.

U.S. Pat. No. 6,737,441 appears to disclose methods of preventing or inhibiting the growth of *Helicobacter pylori* through the use of a composition that comprises a glucosinolate, an isothiocyanate or a derivative or metabolite thereof. The '441 patent also appears to disclose methods of preventing or treating persistent chronic gastritis, ulcers and/or stomach cancer in subjects at risk for, or in need of treatment thereof.

U.S. Pat. No. 6,340,784 appears to disclose a method for producing *Brassica oleracea* with elevated anticarcinogenic glucosinolate derivatives. The elevated levels are obtained by crossing wild *Brassica oleracea* species with *Brassica oleracea* breeding lines, and subsequently selecting hybrids with levels of 4-methylsulfinylbutyl and/or 3-methylsulfinylpropyl glucosinolates elevated above that initially found in *Brassica oleracea* breeding lines. The invention also relates to edible brassica plants, such as broccoli plants, with elevated levels of 4-methylaulfinylbutyl glucosinolate and/or 3-methylsulfinylpropyl glucosinolates, and to seeds of such plants.

U.S. Pat. No. 6,166,003 appears to disclose a compound comprising a heterocyclic moiety, such as a thiophene, covalently attached to an alkylene isothiocyanate moiety. The compound is reportedly effective to prevent the occurrence or progression of cancer or a precancerous condition, and can be used for therapeutic or prophylactic purposes. The compound can be provided and administered in the form of a pharmaceutical composition, a cosmetic, a food additive, supplement, or the like. The '003 patent also discloses methods for synthesis and use of the chemopreventive compound.

U.S. Pat. No. 5,411,986 appears to disclose that sulforaphane has been isolated and identified as a major and very potent phase II enzyme inducer in broccoli (*Brassica oleracea* italica). Sulforaphane is disclosed as a monofunctional inducer, inducing phase II enzymes selectively without the induction of aryl hydrocarbon receptor-dependent cytochromes P-450 (phase I enzymes). The '986 patent discloses synthesizing analogues differing in the oxidation state of sulfur and the number of methylene groups, wherein their inducer potencies were measured. Sulforaphane was identified as the most potent of these analogues. Other analogues having different substituent groups in place of the methylsulfinyl group of sulforaphane were also synthesized and assessed. Of these, the most potent were 6-isothiocyanato-2-hexanone and exo-2-acetyl-6-isothiocyanatonorbornane.

U.S. Pat. No. 5,114,969 appears to disclose a method of inhibiting lung tumor multiplicity and/or incidence by treating mammals with relatively long chain arylalkyl isothiocyanates, especially effective with respect to tumors induced by exposure to tobacco-specific nitrosamine. Among the isothiocyanates disclosed are 4-phenylbutyl isothiocyanate, phenylpentyl isothiocyanate and phenylhexyl isothiocyanate, which are synthesized by adding hydrochloride of phenylbutylamine, phenylpentylamine, or phenylhexylamine in water to thiophosgene in an inert organic solvent.

United States Patent Application Publication No. 2013/0116203 appears to disclose glucosinolate and isothiocyanate compounds and related methods for synthesizing these compounds and analogs. In certain embodiments, these glucosinolate and isothiocyanate compounds are useful and chemopreventive and or chemotherapeutic agents. Examples include compounds of Formula I: R—N=C=S (I) wherein R is selected from the group consisting of dimethylpropyl, $C_3$-$C_{10}$ mono- or bicycloalkyl, $C_6$-$C_{10}$ mono- or bicycloakenyl, halobenzyl, alkyloxybenzyl, tetrahydronaphthalenyl, biphenyl-$C_1$-$C_6$-alkyl, phenoxybenzyl-$C_1$-$C_6$-alkyl, and pyridinyl-$C_1$-$C_6$-alkyl; N-acetyl cysteine conjugates thereof; and salts thereof.

United States Patent Application Publication No. 2009/0081138 appears to disclose chemoprotective compositions containing reduced oil-content extraction meals made from plants containing natural oils and glucosinolates. The oil content of the extraction meals may be reduced using batchwise or continuous supercritical fluid extractions. Also provided are glucosinolate-rich compositions containing purified glucosinolates isolated from plant materials. The glucosinolate-rich compositions may be made by reducing the oil content of a plant materials containing natural oils and glucosinolates and isolating the glucosinolates from the reduced oil-content plant materials using a membrane extraction. Natural oils containing isothiocyanates are also provided.

United States Patent Application Publication No. 2006/0127996 appears to disclose a method of extraction of isothiocyanates into oil from glucosinolate-containing plants and method of producing products with oil containing isothiocyanates extracted from glucosinolate-containing plants.

While some above-identified patents and publications do appear to disclose certain treatments for biofilms and other patents and publications do appear to disclose certain natural, semi-sythentic, and/or synthetic compounds having one or more isothiocyanate functional groups associated with a plurality of applications and/or uses, none of the above-identified patents and/or publications disclose isothiocyanate functional surfactants derived from natural and/or non-natural amino acids, including, but not limited to, lysine. Furthermore, none of the above-identified patents and/or publications disclose the use of isothiocyanate functional surfactants to treat biofilms and human conditions related to the presence of biofilms.

It is therefore an object of the present invention to provide novel isothiocyanate functional surfactants that will partially and/or fully remedy problems and/or complications associated with non-surfactant and/or non-lysine derived isothiocyanate functional compounds. It is therefore an additional object of the present invention to provide novel formulations incorporating isothiocyanate functional surfactants, and associated novel methods of use—including the use of isothiocyanate functional surfactants to treat biofilms and medical conditions related to the presence of biofilms.

These and other objects of the present invention will become apparent in light of the present specification, claims, chemical structures, chemical formulae, and drawings.

SUMMARY OF THE INVENTION

In one embodiment, the present invention is directed to an isothiocyanate functional surfactant used to treat a biofilm, wherein said isothiocyanate functional surfactant comprises at least one isothiocyanate functional group associated with an aliphatic and/or aromatic carbon atom of the isothiocyanate functional surfactant.

The present invention is also directed to a lysine derivative used to treat a biofilm, wherein the lysine derivative comprises an α-nitrogen and a ε-nitrogen, and wherein an alkyl and/or alkanoyl substituent comprising at least approximately 8 carbon atoms is associated with the α-nitrogen, and further wherein at least one isothiocyanate functional group is associated with the ε-nitrogen.

The present invention is further directed to a novel surfactant used to treat a biofilm, wherein the protonated form of said surfactant is represented by the following chemical structure/representation:

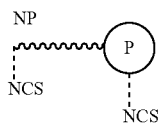

wherein the surfactant comprises a non-polar moiety (NP) and a polar moiety (P), and wherein at least one isothiocyanate functional group (NCS) is associated with the polar and/or non-polar moiety.

In another embodiment, the present invention is directed to a surfactant or a pharmaceutically acceptable salt thereof used to treat a biofilm, wherein the protonated form of said surfactant is represented by the following chemical structure:

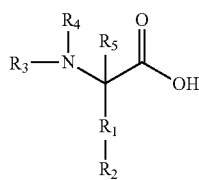

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; and wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom (s).

The present invention is also directed to a surfactant or a pharmaceutically acceptable salt thereof used to treat a biofilm, wherein the protonated form of said surfactant is represented by the following chemical structure:

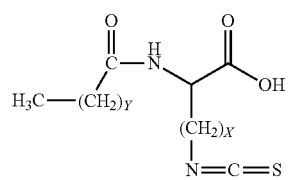

wherein X comprises an integer ranging from approximately 1 to approximately 25, and wherein Y comprises an integer ranging from approximately 6 to approximately 25.

In a preferred embodiment, the present invention is directed to a surfactant or a pharmaceutically acceptable salt thereof used to treat a biofilm, wherein the protonated form of said surfactant is represented by the following chemical structure:

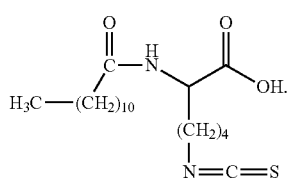

In another embodiment, the present invention is directed to a surfactant or a pharmaceutically acceptable salt thereof used to treat a biofilm, wherein the surfactant is represented by the following chemical structure:

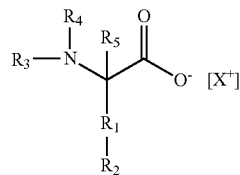

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s), wherein X comprises a counter cation such as, but not limited to, alkali metals, alkaline earth metals, transition metals, s-block metals, d-block metals, p-block metals, $NZ_4+$, wherein Z comprises, H, $R_6$, $OR_6$, and wherein $R_6$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer.

The present invention is also directed to using one or more of the above-identified isothiocyanate functional surfactants to treat a biofilm by applying the isothiocyanate functional surfactant to a surface having a biofilm and/or administering to the patient having and/or affected by a biofilm a composition comprising a therapeutically effective amount of an isothiocyanate functional surfactant. Such administration preferably comprises oral, intravenous, intramuscular, intrathecal, cutaneous, subcutaneous, transdermal, sublingual, buccal, rectal, vaginal, ocular, otical, and/or nasal administration.

DETAILED DESCRIPTION OF THE INVENTION

While this invention is susceptible of embodiment in many different forms, there is shown in the drawings and described herein in detail several specific embodiments with the understanding that the present disclosure is to be considered as an exemplification of the principles of the invention and is not intended to limit the invention to the embodiments illustrated.

As is discussed in greater detail herein, the present invention is directed toward isothiocyanate functional surfactants and/or surfactant formulations. Preferably, these surfactants are used to treat biofilms and diseases related to the presence of biofilms in a patient. The term "treat" or "treating" with regard to a biofilm includes, but is not limited to, removing, releasing, damaging, destroying, degrading, inhibiting growth, and/or physically and/or chemically compromising at least a portion of the biofilm—just to name a few.

It will be understood that the term surfactant is derived from the contraction of the terms surface-active-agent and is defined herein as a molecule and/or group of molecules which are able to modify the interfacial properties of the liquids (aqueous and non-aqueous) in which they are present. The surfactant properties of these molecules reside in their amphiphilic character which stems from the fact that each surfactant molecule has both a hydrophilic moiety and a hydrophobic (or lipophilic) moiety, and that the extent of each of these moieties is balanced so that at concentrations at or below the critical micelle concentration (i.e., CMC) they generally concentrate at the air-liquid interface and materially decrease the interfacial tension. For example, sodium salts of saturated carboxylic acids are extremely soluble in water up to C8 length and are thus not generally regarded as true surfactants. They become less soluble in water from C9 up to C18 length, the domain of effective surfactants for this class of compounds. The carboxylic acids (fatty acids) can be either saturated or unsaturated starting from C16 chain lengths.

Without being bound by any one particular theory, it is believed that the isothiocyanate functional surfactants disclosed herein effectively treat biofilms by modifying and/or penetrating the extracellular polymeric substance (EPS) wall, membrane, and/or barrier. It is also believed that the isothiocyanate functional surfactants disclosed herein facilitate enhanced anti-biofilm activity due to their co-functionality as surfactants having isothiocyanate moieties.

In accordance with the present invention, the isothiocyanate functional surfactants may be used as a leave-on product in which one or more surfactants remain on the surface (e.g., floor, countertop, wall, horizontal and/or vertical surface in a public facility, hospital, school, bathroom, kitchen, etcetera) or skin of a patient and are not immediately and/or ever rinsed off away from the surface or skin. Alternatively, the isothiocyanate functional surfactants of the present invention may be used as a wash in/on and/or apply-and-rinse fashion. For either case, it is preferred that the isothiocyanate functional surfactants be generally mild if applied to porous surfaces and/or human skin (e.g., non-irritating or low-irritating). In particular, anionic N-alkanoyl surfactants derived from amino acids are especially preferred because, while not completely predictable, they have a tendency to be mild. The methods of preparation detailed in this invention employ, but are not limited to, amino acids that possess at least two amine functionalities, at least one of which is converted to an N-alkanoyl functionality, and at least one of which is converted into isothiocyanate functionality. The amino acids include, but are not limited to, the α-amino acids lysine, ornithine, 2,4-diaminobutanoic acid, 2,3-diaminopropionic acid, 2,7-diaminoheptanoic acid, and 2,8-diaminooctanoic acid. Additionally, amino acids other than α-amino acids may be employed, such as β-amino acids, etcetera. It will be understood that amino acid derived surfactants are preferred due to their mild nature, but any one of a number of other surfactants are likewise contemplated for use in accordance with the present invention.

The methods for preparing isothiocyanate functional surfactants and/or their precursors can involve, but are not limited to, conversion of an amine functionality to an isothiocyanate functionality. The methods of conversion of amine functionalities to isothiocyanate functionalities may comprise, but are not limited to: (1) reaction with carbon disulfide to yield an intermediate dithiocarbamate, followed by reaction with ethylchloroformate or its functional equivalent such as bis(trichloromethyl)-carbonate, trichloromethyl chloroformate, or phosgene; (2) reaction with thiophosgene; (3) reaction with 1,1'-thiocarbonyldiimidizole; (4) reaction with phenylthiochloroformate; (5) reaction with ammonium or alkali metal thiocyanate to prepare an intermediate thiourea followed by cleaving to the isothiocyanate via heating; and (6) reaction with an isothiocyanato acyl halide [SCN—$(CH_2)_n$—CO—Cl]. The resulting isothiocyanate functional surfactant, depending on the method of preparation, can be isolated as a pure material or as a mixture with other surfactants. The resulting isothiocyanate functional surfactant, depending on the method of preparation, can be isolated and used directly in nonionic form, anionic form, cationic form, zwitterionic (amphoteric) form, or in a neutral surfactant-precursor form in combination with a base such as sodium hydroxide or triethanol amine if the neutral surfactant-precursor form possesses a protonated carboxylic acid group such that reaction (deprotonation) with the base converts the neutral surfactant-precursor form to an anionic surfactant, or in neutral surfactant-precursor form in combination with an acid if the neutral surfactant-precursor form possess amine functionality such that reaction (protonation) with the acid converts the neutral surfactant-precursor form to a cationic surfactant.

In accordance with the present invention the isothiocyanate functional surfactants can be applied to a surface and/or associated with a human using any one of a number of techniques including, but not limited to, spraying, dripping, dabbing, rubbing, blotting, dipping, and any combination thereof. Moreover, human administration of the relevant surfactants may comprise oral, intravenous, intramuscular, intrathecal, cutaneous, subcutaneous, transdermal, sublingual, buccal, rectal, vaginal, ocular, otical, and/or nasal administration.

In certain preferred embodiments of the present invention, the isothiocyanate functional surfactants are removed from the surface and/or affected area after a period of time. Such a period comprises, but is not limited to, seconds (e.g., 1 second, 2 seconds, 5 seconds, 10 seconds, 15 seconds, 20 seconds, 30 seconds, 45 seconds, and 60 seconds), minutes (e.g., 1 minute, 2 minutes, 5 minutes, 10 minutes, 15 minutes, 20 minutes, 30 minutes, 45 minutes, and 60 minutes), hours (e.g., 1 hour, 2 hours, 5 hours, 10 hours, 15 hours, 20 hours, 30 hours, 45 hours, and 60 hours), days (e.g., 1 day, 2 days, 3 days, 4 days, 5 days, 6 days, 7 days, 10 days, 14 days, 21 days, 30 days), etcetera. It will be understood that the step of removing preferably occurs via rinsing, wiping, and/or extracting—just to name a few.

Depending upon the subject and/or the severity of the medical condition, multiple administration and/or applications may be necessary. As such, the steps of applying and/or removing the isothiocyanate functional surfactants may be repeated once or a plurality of times per day.

In one embodiment, the present invention is directed to an isothiocyanate functional surfactant used to treat a biofilm, wherein said isothiocyanate functional surfactant comprises at least one isothiocyanate functional group associated with an aliphatic and/or aromatic carbon atom of the isothiocyanate functional surfactant.

The present invention is also directed to a lysine derivative used to treat a biofilm, wherein the lysine derivative comprises an α-nitrogen and a ε-nitrogen, and wherein an alkyl and/or alkanoyl substituent comprising at least approximately 8 carbon atoms is associated with the α-nitrogen, and further wherein at least one isothiocyanate functional group is associated with the ε-nitrogen.

The present invention is further directed to a novel surfactant used to treat a biofilm, wherein the protonated form of said surfactant is represented by the following chemical structure/representation:

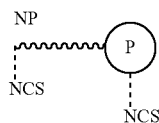

wherein the surfactant comprises a non-polar moiety (NP) and a polar moiety (P), and wherein at least one isothiocyanate functional group (NCS) is associated with the polar and/or non-polar moiety.

In another embodiment, the present invention is directed to a surfactant or a pharmaceutically acceptable salt thereof used to treat a biofilm, wherein the protonated form of said surfactant is represented by the following chemical structure:

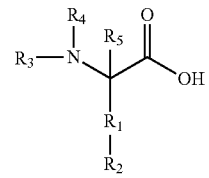

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; and wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s).

The present invention is also directed to a surfactant or a pharmaceutically acceptable salt thereof used to treat a biofilm, wherein the protonated form of said surfactant is represented by the following chemical structure:

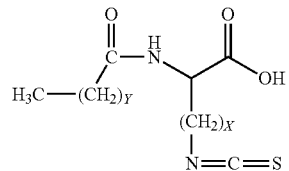

wherein X comprises an integer ranging from approximately 1 to approximately 25, and wherein Y comprises an integer ranging from approximately 6 to approximately 25.

More preferably, the surfactant is represented by one or more of the following chemical structures:

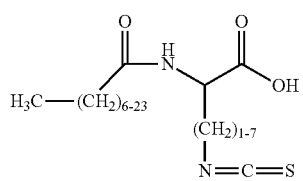

-continued

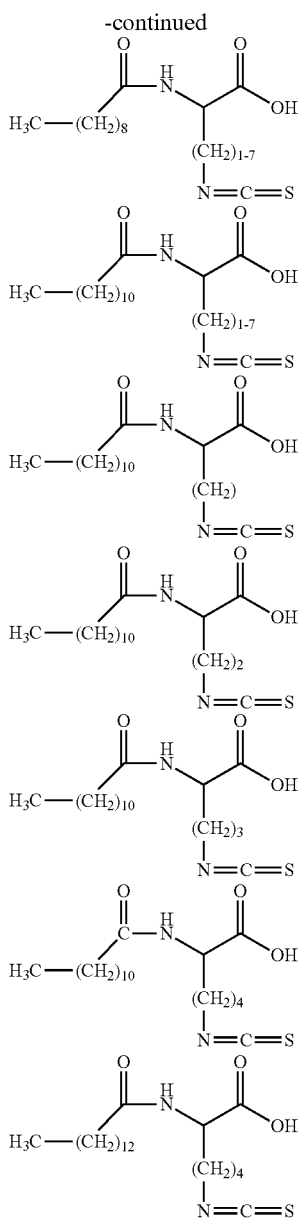

In another embodiment, the present invention is directed to a surfactant or a pharmaceutically acceptable salt thereof used to treat a biofilm,
wherein the protonated form of the surfactant is represented by the following chemical structure:

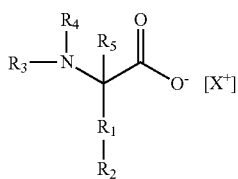

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s), wherein X comprises a counter cation such as, but not limited to, alkali metals, alkaline earth metals, transition metals, s-block metals, d-block metals, p-block metals, $NZ_4+$, wherein Z comprises, H, $R_6$, $OR_6$, and wherein $R_6$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer.

In accordance with the present invention, the isothiocyanate functional surfactant may be associated with an additional surfactant, wherein the additional surfactant is selected from at least one of the group comprising a nonionic surfactant, an anionic surfactant, a cationic surfactant, a zwitterionic surfactant, and combinations thereof.

Non-limiting examples of preferred anionic surfactants include taurates; isethionates; alkyl and alkyl ether sulfates; succinamates; alkyl sulfonates, alkylaryl sulfonates; olefin sulfonates; alkoxy alkane sulfonates; sodium and potassium salts of fatty acids derived from natural plant or animal sources or synthetically prepared; sodium, potassium, ammonium, and alkylated ammonium salts of alkylated and acylated amino acids and peptides; alkylated sulfoacetates; alkylated sulfosuccinates; acylglyceride sulfonates, alkoxyether sulfonates; phosphoric acid esters; phospholipids; and combinations thereof. Specific anionic surfactants contemplated for use include, but are by no means limited to, ammonium cocoyl isethionate, sodium cocoyl isethionate, sodium lauroyl isethionate, sodium stearoyl isethionate, sodium lauroyl sarcosinate, sodium cocoyl sarcosinate, sodium lauryl sarcosinate, disodium laureth sulfosuccinate, sodium lauryl sulfoacetate, sodium cocoyl glutamate, TEA-cocoyl glutamate, TEA cocoyl alaninate, sodium cocoyl taurate, potassium cetyl phosphate.

Non-limiting examples of preferred cationic surfactants include alkylated quaternary ammonium salts $R_4NX$; alkylated amino-amides ($RCONH$—$(CH_2)_n$)$NR_3X$; alkylimidazolines; alkoxylated amines; and combinations thereof. Specific examples of anionic surfactants contemplated for use include, but are by no means limited to, cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, distearyl methyl ammonium chloride, distearyl methyl ammonium bromide, ditallow dimethyl ammonium chloride, ditallow dimethyl ammonium sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-imonium chloride phosphate, stearamidopropyl ethyldimonium ethosulfate, stearimidopropyldimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, ditallowyl oxyethyl dimethyl ammonium chloride, behenamidopropyl PG dimonium chloride, dilauryl dimethyl ammonium chloride, distearly dimethyl ammonium chloride, dimyristyl dimethyl ammonium chloride, dipalmityl dimethyl ammonium chloride, distearyl dimethyl ammonium chloride, stearamidoproyl PG-dimonium chloride phosphate, stearamidopropyl ethyldiammonium ethosulfate, stearamidopropyl dimethyl (myristyl acetate) ammonium chloride, stearimidopropyl dimethyl cetaryl ammonium tosylate, stearamido propyl dimethyl ammonium chloride, stearamidopropyl dimethyl ammonium lactate.

Non-limiting examples of preferred non-ionic surfactants include alcohols, alkanolamides, amine oxides, esters (including glycerides, ethoxylated glycerides, polyglyceryl esters, sorbitan esters, carbohydrate esters, ethoxylated carboxylic acids, phosphoric acid triesters), ethers (including ethoxylated alcohols, alkyl glucosides, ethoxylated polypropylene oxide ethers, alkylated polyethylene oxides, alkylated polypropylene oxides, alkylated PEG/PPO copolymers), and silicone copolyols. Specific examples of non-ionic surfactants contemplated for use include, but are by no means limited to, cetearyl alcohol, ceteareth-20, nonoxynol-9, C12-15 pareth-9, POE(4) lauryl ether, cocamide DEA, glycol distearate, glyceryl stearate, PEG-100 stearate, sorbitan stearate, PEG-8 laurate, polyglyceryl-10 trilaurate, lauryl glucoside, octylphenoxy-polyethoxyethanol, PEG-4 laurate, polyglyceryl diisostearate, polysorbate-60, PEG-200 isostearyl palmitate, sorbitan monooleate, polysorbate-80.

Non-limiting examples of preferred zwitterionic or amphoteric surfactants include betaines; sultaines; hydroxysultaines, amido betaines, amidosulfo betaines; and combinations thereof. Specific examples of amphoteric surfactants contemplated for use include, but are by no means limited to, cocoamidopropyl sultaine, cocoamidopropyl hydroxyl sultaine, cocoamidopropylbetaine, coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl (2-bishydroxy) carboxymethyl betaine, stearyl bis-(2-hydroxyethyl) carboxymethyl betaine, oelyl dimethyl gamma-carboxypropyl betaine, lauryl bis-(2-hydroxypropyl)alpha carboxymethyl betaine, coco dimethyl sulfopropyl betaine, stearyl dimethyl sulfopropyl betaine, lauryl dimethyl sulfoethyl betaine, lauryl bis(2-hydroxyethyl) sulfopropyl betaine, oleyl betaine, cocamidopropyl betaine.

In further accordance with the present invention, the isothiocyanate functional surfactant may be incorporated into a formulation comprising one or more solvents. Preferably, the solvent comprises a hydrocarbon and/or silicone oil that is generally non-hygroscopic and/or generally hydrophobic. Suitable examples, include, silicone based solvents and/or fluids, mineral oil, vegetable oils, squalene (i.e., 2,6,10,15,19,23-hexamethyltetracosane)—just to name a few. However, when treating a biofilm on a surface, such as a hospital surface, then a deprotonated form of the isothiocyanate functional surfactant may be incorporated into a polar and/or aqueous formulation.

The invention is further described by the following examples.

EXAMPLE I

Preparation of a mixture of $N_\alpha$-lauroyl-$N_\varepsilon$-isothiocyanato-L-Lysine with $N_\alpha,N_\varepsilon$-bis-lauroyl-L-lysine A 1 liter beaker equipped with an overhead mechanical stainless steel paddle stirrer was charged with 100 mL of 1 M NaOH (0.100 mol). Stirring was begun and the beaker cooled to −5° C. to −10° C. using a salt/ice bath. Next, 23.4 g (0.100 mol) of $N_\varepsilon$-benzylidene-L-lysine (prepared via the method of Bezas, B and Zervas, L., JACS, 83, 1961, 719-722) was added. Immediately afterward and while keeping the solution cold, 140 mL (0.140 mol) of precooled (in a salt/ice bath) 1 M NaOH and 26.1 mL of lauroyl chloride was added in two equal portions over a period of 6 minutes. The mixture was stirred for 10 more minutes at −5 to −10° C., then the ice bath was removed and the reaction mixture allowed to stir for another 1 hour while warming to room temperature. Next, the reaction mixture was cooled using a salt/ice bath and then sufficient concentrated HCl was added to adjust the pH to 7.5-7.8. With the pH at 7.8-7.8 and with continued cooling and stirring, 4.6 mL (60% of stoichiometric, 0.068 mol) of thiophosgene was added dropwise via an additional funnel over the period of 1 hour. During this time, sufficient 1 M NaOH was added to maintain a pH range between 7.5-7.8. After the thiophosgene addition was complete, additional 1 M NaOH was added as necessary until the pH stabilized in 7.5-7.8 range. Next, sufficient 30% NaOH was added to adjust the pH to approximately 8.5. Next, 12 mL (0.051 mol) of lauroyl chloride was rapidly added, followed by sufficient 1 M NaOH to keep the pH in the range of 8.00-8.50. Next, sufficient concentrated HCl was added to adjust the pH to 1.5. The reaction mixture was filtered via vacuum filtration, and the precipitate washed with dilute HCl (pH=2). The product, a white moist solid, was dried in vacuo while heating to 60° C. 45.19 g of white solid product was recovered, a mixture of predominantly $N_\alpha$-lauroyl-$N_\varepsilon$-isothiocyanato-L-lysine and $N_\alpha,N_\varepsilon$-bis-lauroyl-L-lysine (determined via LC-MS analysis). Both compounds in this mixture can be simultaneously converted into anionic (carboxylate) surfactants via reaction with aqueous NaOH to yield a clear aqueous solution of the surfactants.

EXAMPLE II

Preparation of Pure $N_\alpha$-lauroyl-$N_\varepsilon$-isothiocyanato-L-Lysine

Step 1: Preparation of $N_\alpha$-lauroyl-$N_\varepsilon$-carbobenzoxy-L-Lysine 60.0 g of $N_\varepsilon$-cbz-L-Lysine (cbz is carbobenzoxy) purchased from Atomole Scientific Company, LTD was added to a three-liter beaker along with 1200 mL of RO water and the mixture was stirred. Next, 39 mL of 30% aqueous NaOH was added, resulting in dissolution of the $N_\varepsilon$-cbz-L-Lysine. The resulting solution was cooled in an ice bath and then 52.5 mL of lauroyl chloride was added. The ice bath was removed 30 minutes later, and stirring continued for an additional six hours, at which time 18 mL of concentrated hydrochloric acid was added. The reaction mixture was then filtered via vacuum filtration, the white solid product washed with 1 M aqueous HCl, and then the solid product was dried in vacuo while heated to approximately 85° C. 96.5 g of dry white solid product was obtained. The product can be further purified by dissolving it in methanol, filtering off any insoluble precipitate, and removing the methanol in vacuo to recover a white solid product (mp 99.5-103.0° C.)

Step 2: Preparation of $N_\alpha$-lauroyl-$N_\varepsilon$-ammonium chloride-L-Lysine 10.0 g of $N_\alpha$-lauroyl-$N_\varepsilon$-carbobenzoxy-L-Lysine was weighed into a one liter Erlenmeyer flask equipped with a magnetic stir bar. 150 mL of concentrated hydrochloric acid was added and the solution was stirred and heated in an oil bath to 104° C., then allowed to cool with the oil bath back to room temperature. The solution was then cooled to 9° C. for approximately four hours, during which time a large mass of white precipitate formed. The reaction mixture was filtered in vacuo and rinsed with a small amount of cold 1 M HCl. The white solid reaction product was then dried in vacuo while being heated to 78° C., yielding 7.89 g of white solid product (mp 191-193° C.).

Step 3: Preparation of $N_\alpha$-lauroyl-$N_\varepsilon$-isothiocyanato-L-Lysine 0.46 mL of thiophosgene was added to 30 mL of dichloromethane in a 125 mL Erlenmeyer flask equipped with a magnetic stir bar. To this solution was drop wise added over 15 minutes a solution consisting of 2.00 g $N_\alpha$-lauroyl-$N_\varepsilon$-ammonium chloride-L-Lysine, 10 mL RO water, and 2.7 mL 20% aqueous NaOH. Stirring was continued for an additional 30 minutes, after which sufficient concentrated hydrochloric acid was added to lower the pH to 1 as indicated by testing with pHydrion paper. The reaction solution was then transferred into a separatory funnel and the bottom turbid dichloromethane layer was isolated and dried with anhydrous magnesium sulfate and gravity filtered. To the filtrate was added 50 mL of hexanes. The solution was then concentrated via removal of 34 mL of solvent via trap-to-trap distillation and then placed in a −19° C. freezer. A mass of white precipitate formed after a few hours and was isolated via vacuum filtration and then dried in vacuo for 2 hours. 1.130 g of a slightly off white solid powder product was obtained [mp 37.0-39.0° C.; IR (cm$^{-1}$), 3301sb, 2923s, 2852s, 2184m, 2099s, 1721s, 1650s, 1531s, 1456m, 1416w, 1347m, 1216m, 1136w]

EXAMPLE III

Preparation of a Two-Part Formulation

A two-part formulation for topical application to the skin was prepared as follows:

Part I: A 25% by mass mixture of $N_\alpha$-lauroyl-$N_\varepsilon$-isothiocyanato-L-Lysine in Dow Corning DC344 fluid (a mixture of octamethyl-cyclotetrasiloxane and decamethyl-cyclopentasiloxane) was prepared in a mortar and pestle to produce a paste that was loaded into a 5 ml plastic disposable syringe. A syringe needle was not employed. Rather, the dispensing end of the syringe was capped except for when dispensing without a syringe needle into the palm of a hand occurred.

Part II: Part II consisted of Cetaphil Moisturizing Lotion to which additional triethanol amine (TEA) was added such that the concentration of the additional triethanol amine was 0.006 g triethanol amine per gram of lotion, raising the pH of the Cetaphil Lotion from 7.74 to 8.77.

Preferred Instructions for Application of Formulation to the Skin: A 0.2 mL portion of the $N_\alpha$-lauroyl-$N_\varepsilon$-isothiocyanato-L-Lysine/DC344 mixture is dispensed from the syringe into the palm of a hand (approximately 0.13 g of the mixture). Next, two full squirts of the Cetaphil/TEA lotion is dispensed on top of the $N_\alpha$-lauroyl-$N_\varepsilon$-isothiocyanato-L-Lysine/DC344 mixture (approximately 2.8 g of the lotion). Next, using the index finger of the other hand, the components are mixed thoroughly for 30 seconds, during which time the water insoluble $N_\alpha$-lauroyl-$N_\varepsilon$-isothiocyanato-L-Lysine surfactant-precursor is deprotonated to yield the water-soluble anionic (carboxylate) surfactant and yield a homogenous smooth white lotion (this reduces the pH to 7.4). This mixture is then applied to the afflicted areas by gently rubbing it on as one would apply any moisturizing lotion.

EXAMPLE IV

Preparation of a One-Part Formulation

A one-part formulation for topical application to the skin was prepared as follows:

First, 0.00025% (by wt.; 5.0 micromolar) of Sodium $N_\alpha$-lauroyl-$N_\varepsilon$-isothiocyanate-L-Lysinate, the sodium salt of the material provided in step three of Example II, was associated with (QS to achieve 100%) 2,6,10,15,19,23-Hexamethyltetracosane (commercially available from Sigma-Aldrich). It will be understood that the concentration of Sodium $N_\alpha$-lauroyl-$N_\varepsilon$-isothiocyanate-L-Lysinate may range from approximately 0.000001% to approximately 50%. Non-limiting examples of additional concentrations include 0.0005%, 0.005%, 0.005%, 0.005%, 0.05%, 0.5%, 5%—just to name a few.

Preferred Instructions for Application of the One-Part Formulation to the skin: A 0.1-1.0 mL portion of the one-part formulation is dispensed from a container into the palm of a hand for subsequent administration to an affected area and/or is dispensed directly onto an affected area by gently rubbing it on as one would apply a moisturizing lotion.

The foregoing description merely explains and illustrates the invention and the invention is not limited thereto except insofar as the appended claims are so limited, as those skilled in the art who have the disclosure before them will be able to make modifications without departing from the scope of the invention.

What is claimed and desired to be secured by Letters Patent of the United States is:

1. A method, comprising the step of administering to a patient having a biofilm an isothiocyanate functional surfactant, wherein the surfactant comprises a lysine derivative having an α-nitrogen and a ε-nitrogen, and wherein an alkyl substituent comprising at least 8 carbon atoms is bound to the α-nitrogen, and further wherein the ε-nitrogen forms part of an isothiocyanate functional group.

2. The method according to claim 1, wherein the composition comprising the isothiocyanate functional surfactant is administered to the patient at least one of orally, intravenously, intramuscularly, intrathecally, cutaneously, subcutaneously, transdermally, sublingually, buccally, rectally, vaginally, ocularly, otically, and nasally.

3. The method according to claim 1, wherein the composition comprising the isothiocyanate functional surfactant is topically administered to the patient.

4. The method according to claim 3, wherein the amount of isothiocyanate functional surfactant in the composition topically administered to the patient ranges from approximately 0.5 nmol/cm2 to approximately 10 μmol/cm2.

5. The method according to claim 4, wherein the composition comprising the isothiocyanate functional surfactant is a topical preparation selected from the group consisting of ointment, cream, emulsion, lotion and gel.

6. The method according to claim 5, wherein the composition further comprises one or more pharmaceutical, biological or molecular biological active agents.

7. The method according to claim 1, wherein the patient is a mammal.

8. The method according to claim 1, wherein the mammal is a human.

* * * * *